(12) United States Patent
Shinde et al.

(10) Patent No.: US 12,004,785 B2
(45) Date of Patent: Jun. 11, 2024

(54) RETROGRADE FEMORAL INTRAMEDULLARY NAIL, AND RELATED SYSTEMS AND METHODS

(71) Applicant: DEPUY SYNTHES PRODUCTS, INC., Raynham, MA (US)

(72) Inventors: Rohit Shinde, Irvine, CA (US); Thomas Keyer, West Chester, PA (US); David Cowens, West Chester, PA (US); Joshua McManus, Downingtown, PA (US); Raymond Schmitt, West Chester, PA (US); Michael Bushelow, West Chester, PA (US); Stanley J. Kmiec, Jr., Morgantown, PA (US); Josef Gabelberger, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/725,865

(22) Filed: Apr. 21, 2022

(65) Prior Publication Data
US 2023/0338066 A1    Oct. 26, 2023

(51) Int. Cl.
*A61B 17/72*    (2006.01)
*A61B 17/17*    (2006.01)
*A61B 17/74*    (2006.01)

(52) U.S. Cl.
CPC ...... *A61B 17/7241* (2013.01); *A61B 17/1725* (2013.01); *A61B 17/744* (2013.01)

(58) Field of Classification Search
CPC ............ A61B 17/7241; A61B 17/1725; A61B 17/744

USPC ...................................................... 606/62–68
See application file for complete search history.

(56) References Cited

U.S. PATENT DOCUMENTS

| | | | |
|---|---|---|---|
| 3,433,220 A | 3/1969 | Zickel | |
| 4,475,545 A | 10/1984 | Ender | |
| 4,622,959 A | 11/1986 | Marcus | |
| 4,784,124 A * | 11/1988 | Kaltenbrunner | ..... A61B 17/164 606/63 |
| 4,827,917 A | 5/1989 | Brumfield | |
| 4,846,162 A | 7/1989 | Moehring | |
| 5,034,013 A | 7/1991 | Kyle et al. | |
| 5,035,697 A | 7/1991 | Frigg | |
| 5,041,115 A | 8/1991 | Frigg et al. | |

(Continued)

FOREIGN PATENT DOCUMENTS

| | | |
|---|---|---|
| DE | 199205200 U1 | 10/1992 |
| DE | 20002988 U1 | 6/2000 |

(Continued)

*Primary Examiner* — Eduardo C Robert
*Assistant Examiner* — Tara Rose E Carter
(74) *Attorney, Agent, or Firm* — BakerHostetler

(57) ABSTRACT

A retrograde intramedullary nail for insertion in the medullary canal of a femur includes a body that is elongate and defines a leading end and a trailing end spaced from each other at a length sufficient to extend from an intercondylar region at least to a subtrochanteric region of the femur. The body further defines a leading portion that extends to the leading end. The leading portion defines at least one locking hole configured to receive a fixation member. The at least one locking hole defines a central hole axis that is oriented to extend through the neck and head of the femur.

14 Claims, 9 Drawing Sheets

(56) References Cited

U.S. PATENT DOCUMENTS

| | | |
|---|---|---|
| 5,167,663 A | 12/1992 | Brumfield |
| 5,312,406 A | 5/1994 | Brumfield |
| 5,549,610 A | 8/1996 | Russell et al. |
| 5,573,536 A | 11/1996 | Grosse et al. |
| 5,620,445 A | 4/1997 | Brosnahan et al. |
| 5,697,930 A | 12/1997 | Itoman et al. |
| 5,779,705 A | 7/1998 | Matthews |
| 5,855,579 A | 1/1999 | James et al. |
| 5,935,127 A | 8/1999 | Border |
| 6,010,506 A | 1/2000 | Gosney et al. |
| 6,120,504 A | 9/2000 | Brumback et al. |
| 6,123,708 A | 9/2000 | Kilpela et al. |
| 6,126,661 A | 10/2000 | Faccioli et al. |
| 6,210,414 B1 | 4/2001 | Lin |
| 6,214,013 B1 | 4/2001 | Lambrecht et al. |
| 6,221,074 B1 | 4/2001 | Cole et al. |
| 6,228,086 B1 | 5/2001 | Wahl et al. |
| 6,270,499 B1* | 8/2001 | Leu ................ A61B 17/72 606/62 |
| 6,299,648 B1 | 10/2001 | Doubler et al. |
| 6,402,753 B1 | 6/2002 | Cole et al. |
| 6,406,477 B1 | 6/2002 | Fujiwara |
| 6,443,954 B1 | 9/2002 | Bramlet et al. |
| 6,461,360 B1 | 10/2002 | Adam |
| 6,524,313 B1 | 2/2003 | Fassier et al. |
| 6,855,146 B2 | 2/2005 | Frigg et al. |
| 6,932,818 B2 | 8/2005 | Behrens |
| 7,018,380 B2 | 3/2006 | Cole |
| 7,041,104 B1 | 5/2006 | Cole et al. |
| 7,455,673 B2 | 11/2008 | Gotfried |
| 7,670,340 B2 | 3/2010 | Brivio et al. |
| 7,763,023 B2 | 7/2010 | Gotfried |
| 7,776,038 B2 | 8/2010 | Prien |
| 7,842,036 B2 | 11/2010 | Phillips |
| 7,867,231 B2 | 1/2011 | Cole |
| 7,914,532 B2 | 3/2011 | Shaver et al. |
| D638,125 S | 5/2011 | Velikov |
| D638,126 S | 5/2011 | Velikov |
| 7,947,043 B2 | 5/2011 | Mutchler |
| 8,137,348 B2 | 3/2012 | Gotfried |
| 8,157,803 B1 | 4/2012 | Zirkle, Jr. et al. |
| 8,257,361 B2 | 9/2012 | Ritchey et al. |
| 8,317,788 B2 | 11/2012 | Kaup |
| 8,353,910 B2 | 1/2013 | Dell'Oca |
| 8,394,103 B2 | 3/2013 | O'Reilly et al. |
| 8,409,205 B2 | 4/2013 | Yang et al. |
| 8,449,544 B2 | 5/2013 | Grusin |
| 8,540,714 B2 | 9/2013 | Gordon et al. |
| D693,470 S | 11/2013 | Fagan |
| 8,632,543 B2 | 1/2014 | Metzinger et al. |
| 8,652,136 B2 | 2/2014 | Yang |
| 8,668,695 B2 | 3/2014 | Schwammberger et al. |
| 8,679,121 B2 | 3/2014 | Czartoski et al. |
| 8,734,448 B2 | 5/2014 | Thakkar |
| 8,758,345 B2 | 6/2014 | Sidebotham |
| 8,790,343 B2 | 7/2014 | McClellan et al. |
| 8,834,469 B2 | 9/2014 | Watanabe et al. |
| 8,906,023 B2 | 12/2014 | Matityahu et al. |
| 9,011,444 B2 | 4/2015 | Primiano et al. |
| 9,044,283 B2 | 6/2015 | Simon |
| 9,072,552 B2 | 7/2015 | Simon et al. |
| 9,220,544 B2 | 12/2015 | Matityahu et al. |
| 9,301,767 B2 | 4/2016 | Ritchey et al. |
| 9,308,031 B2 | 4/2016 | Elghazaly et al. |
| 9,320,551 B2 | 4/2016 | Frank et al. |
| 9,333,018 B2 | 5/2016 | Russell et al. |
| 9,358,049 B2 | 6/2016 | Simon et al. |
| 9,408,645 B2 | 8/2016 | Graca et al. |
| 9,427,266 B2 | 8/2016 | Kmiec, Jr. |
| 9,433,449 B2 | 9/2016 | Vega et al. |
| 9,439,695 B2 | 9/2016 | Wolter |
| 9,775,661 B2 | 10/2017 | Rabiner et al. |
| RE47,149 E | 12/2018 | Primiano et al. |
| 2006/0095039 A1* | 5/2006 | Mutchler ............ A61B 17/72 606/64 |
| 2006/0106389 A1* | 5/2006 | Reber ............ A61B 17/8625 606/62 |
| 2007/0276385 A1 | 11/2007 | Schlienger et al. |
| 2007/0288017 A1 | 12/2007 | Kaup |
| 2008/0009873 A1 | 1/2008 | Yacoubian |
| 2008/0294164 A1* | 11/2008 | Frank ............ A61B 17/744 606/301 |
| 2010/0152740 A1 | 6/2010 | O'Reilly et al. |
| 2010/0179551 A1 | 7/2010 | Keller et al. |
| 2012/0143192 A1 | 6/2012 | Watanabe et al. |
| 2012/0221005 A1 | 8/2012 | Corneille et al. |
| 2014/0052132 A1 | 2/2014 | Matityahu et al. |
| 2014/0330274 A1 | 11/2014 | Matityahu et al. |
| 2014/0378973 A1 | 12/2014 | Mueckter |
| 2015/0112345 A1 | 4/2015 | Boraiah |
| 2015/0182266 A1 | 7/2015 | Jakob et al. |
| 2015/0265323 A1 | 9/2015 | Sems et al. |
| 2016/0166264 A1 | 6/2016 | Ritchey et al. |
| 2016/0256202 A1 | 9/2016 | Halder |
| 2019/0038326 A1 | 2/2019 | Hedgeland et al. |
| 2020/0113609 A1 | 4/2020 | Aneja et al. |
| 2021/0015526 A1 | 1/2021 | Oberli et al. |

FOREIGN PATENT DOCUMENTS

| | | |
|---|---|---|
| DE | 102007016459 A1 | 10/2008 |
| EP | 355411 A1 | 2/1990 |
| EP | 1199995 B1 | 9/2007 |
| EP | 1654993 B1 | 1/2008 |
| EP | 1053718 B1 | 7/2008 |
| EP | 1974681 B1 | 6/2010 |
| EP | 1495733 B1 | 9/2010 |
| EP | 1859751 B1 | 9/2010 |
| EP | 1867294 B1 | 9/2010 |
| EP | 2109404 B1 | 1/2012 |
| EP | 1948049 B1 | 5/2012 |
| EP | 2341854 B1 | 9/2013 |
| EP | 2349040 B1 | 8/2014 |
| EP | 2712562 B1 | 7/2015 |
| EP | 2672909 B1 | 10/2015 |
| EP | 2783649 B1 | 5/2016 |
| EP | 2755580 B1 | 6/2016 |
| EP | 2672910 B1 | 7/2016 |
| GB | 2445346 B | 3/2011 |
| JP | 2000-342596 A | 12/2000 |
| WO | 2000076414 A1 | 12/2000 |
| WO | 2007048038 A2 | 4/2007 |
| WO | 2008094407 A1 | 8/2008 |
| WO | 2010014694 A1 | 2/2010 |
| WO | 2010043380 A1 | 4/2010 |
| WO | 2012107056 A1 | 8/2012 |
| WO | 2012107226 A1 | 8/2012 |
| WO | 2013037386 A1 | 3/2013 |
| WO | 2015106319 A2 | 7/2015 |
| WO | 2016042148 A1 | 3/2016 |
| WO | 2016131094 A1 | 8/2016 |
| WO | 2016151611 A1 | 9/2016 |
| WO | 2017121772 A1 | 7/2017 |
| WO | 2018172974 A1 | 9/2018 |

* cited by examiner

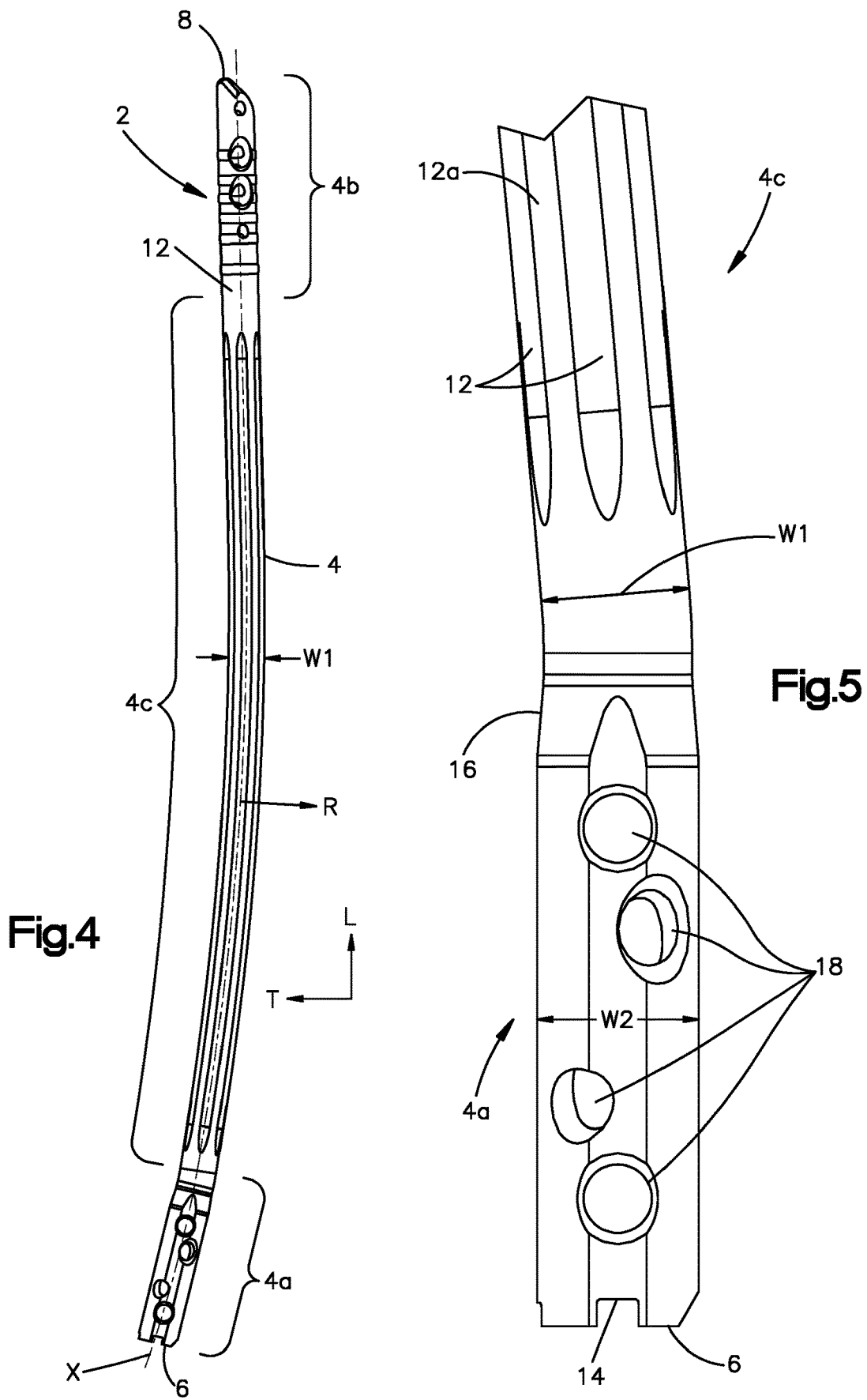

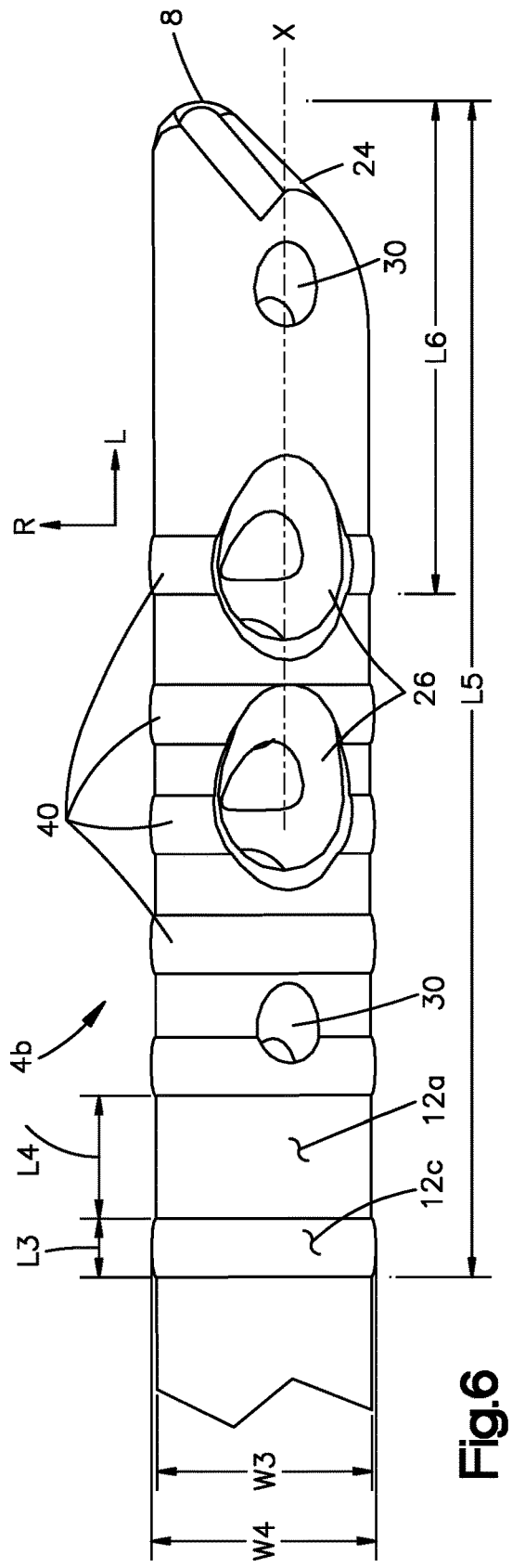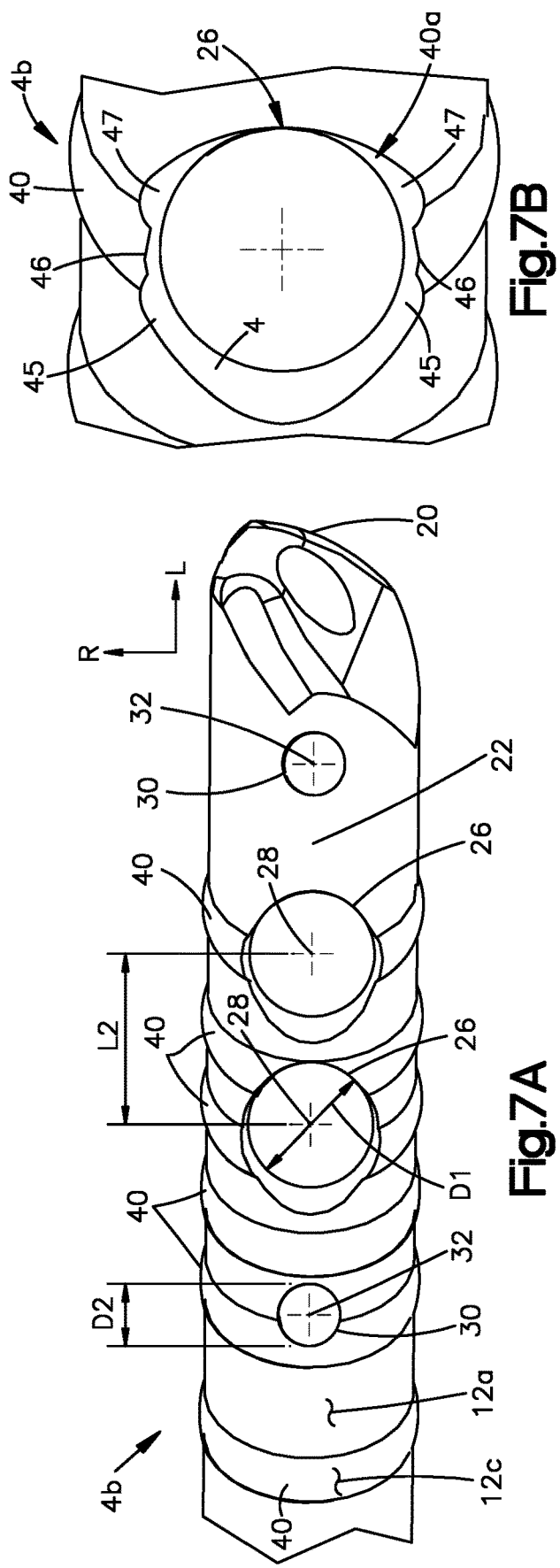

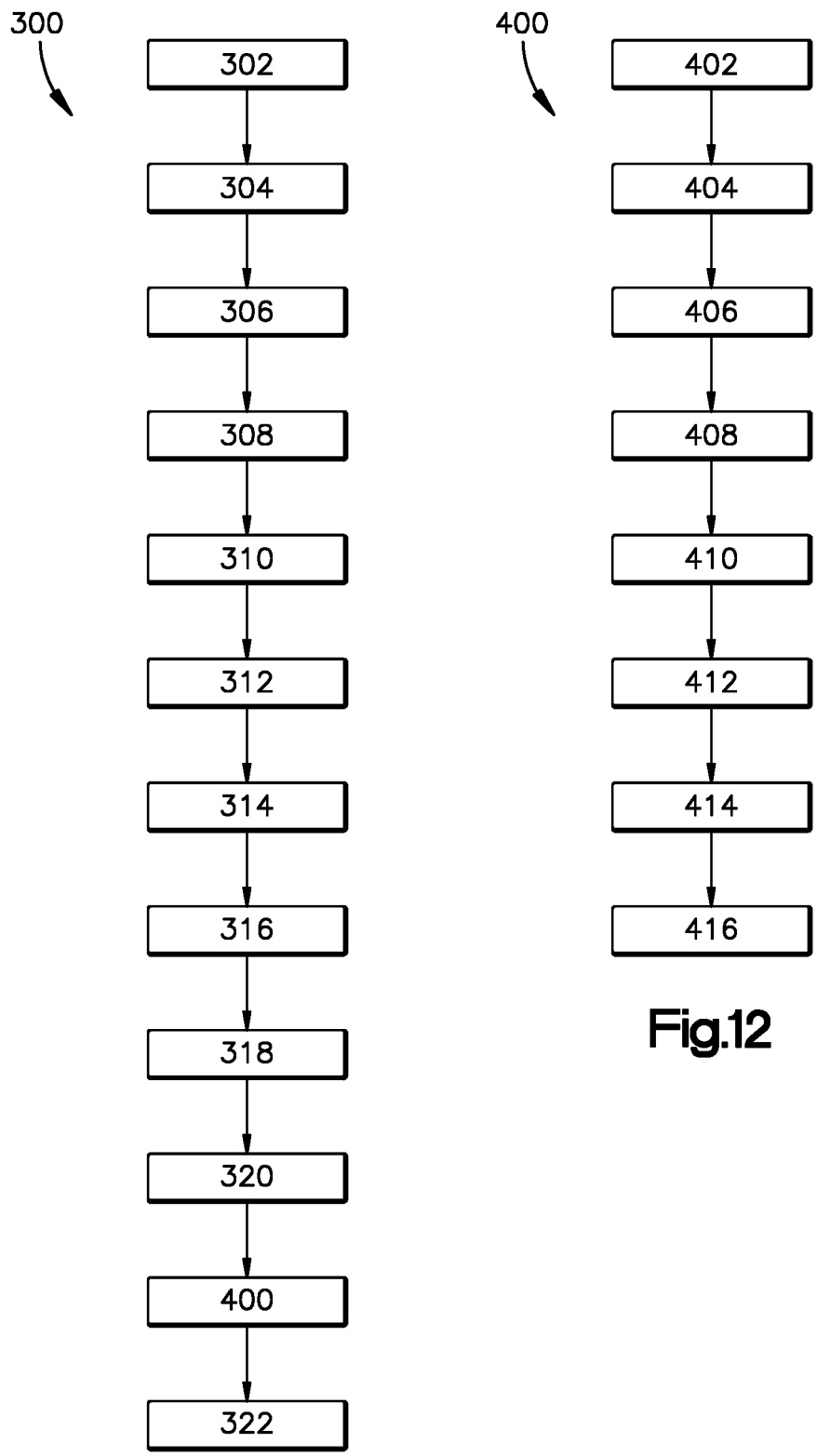

RETROGRADE FEMORAL INTRAMEDULLARY NAIL, AND RELATED SYSTEMS AND METHODS

TECHNICAL FIELD

The present invention relates to devices and instrumentalities for inserting an intramedullary nail within the medullary canal of a longbone, such as a femur, along a retrograde insertion trajectory.

BACKGROUND

Femoral fractures are often treated with screws or other fixation devices inserted into or through a bone to stabilize fractured portions thereof once they have been brought into corrective alignment. Femoral trochanteric bone fixation treatments comprise the insertion of an intramedullary nail into the medullary cavity of the femur and a subsequent insertion of a bone fixation screw into a condylar portion of the femur at an angle relative to the intramedullary nail (i.e., along an axis of the femoral neck and center of the femoral head).

Femoral intramedullary nails are typically designed for either an antegrade or retrograde insertion trajectory into the medullary canal. Antegrade insertion trajectories extend from the anatomical proximal end of the femur (i.e., at the hip joint), such as from the tip or slightly lateral to the tip of the greater trochanter, and into the medullary canal toward the anatomical distal end of the femur along the anatomical axis of the femur. Retrograde insertion trajectories extend from the anatomical distal end of the femur (i.e., at the knee joint) toward the anatomical proximal end of the femur and are effectively the opposite of antegrade insertion trajectories.

As used herein, the term "retrograde intramedullary nail" refers to an intramedullary nail designed for retrograde insertion into the medullary canal. Retrograde intramedullary nails are known to provide advantageous fixation to the distal portions of the femur (e.g., the distal condylar and intercondylar regions), such as for treating distal femur fractures. For example, retrograde intramedullary nails allow for easier targeting and insertion of locking screws within locking holes at the trailing end of the nail, which resides within the distal femur. The targeting and insertion of locking nails screws at the trailing end of the nail is simplified by the fact that the trailing end can be directly engaged with instrumentation, such as an insertion handle and/or an aiming arm having aiming elements for targeting the locking holes near the trailing end of the nail. Targeting the locking holes at the trailing end of the retrograde nail (at the distal femur) is further simplified by the fact that the trailing end experiences less deflection and/or deformation than the leading end (at the proximal femur), particularly as the nail length increases. Targeting locking holes at the leading end of a retrograde intramedullary nail, however, is more challenging due to factors such as nail deflection resulting from stress and strain, particularly as the length of the nail increases, and also due to manufacturing tolerances in the nail bend shape. Stress and strain at the leading end of the nail can be exacerbated while "locking" the leading end (i.e., targeting and inserting fixation members, such as bone screws, through locking holes at the leading end).

SUMMARY

According to an embodiment of the present disclosure, a retrograde intramedullary nail for retrograde insertion in the medullary canal of a femur includes a body that is elongate and defines a leading end and a trailing end spaced from each other at a length sufficient to extend from an intercondylar region at least to a subtrochanteric region of the femur. The body further defines a leading portion that extends to the leading end. The leading portion defines at least one locking hole configured to receive a fixation member. The at least one locking hole defines a central hole axis that is configured to extend through the neck of the femur and intersect the head of the femur.

According to another embodiment of the present disclosure, a system for femoral fixation includes an intramedullary nail having a body that is elongate and defines a leading end and a trailing end spaced from each other at a length sufficient to extend from an intercondylar region of the femur at least to a subtrochanteric region of the femur. A leading portion of the body extends to the leading end and defines at least one locking hole configured to receive at least one fixation member for affixing the leading portion to the femur. The leading portion also defines at least one relief formation configured to reduce stress concentrations in the leading portion. The system includes an aiming assembly configured to connect to the leading portion and insert at least one fixation member through the at least one locking hole.

According to an additional embodiment of the present disclosure, a method includes advancing an intramedullary nail within a medullary canal of a femur along a retrograde insertion trajectory, thereby positioning a trailing end of the intramedullary nail within an intercondylar region of the femur while concurrently positioning a leading end of the intramedullary nail within or anatomically proximal to a subtrochanteric region of the femur and aligning at least one locking hole defined by the nail with one or more regions of the femur that include the subtrochanteric region, a transtrochanteric region, a trochanteric region, and an intracapsular region.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 4 is a side view of the intramedullary nail illustrated in FIG. 3;

FIG. 5 is an enlarged view of a trailing portion of the intramedullary nail illustrated in FIG. 4;

FIG. 6 is an enlarged view of a leading portion of the intramedullary nail illustrated in FIG. 4;

FIG. 7A is a perspective view of the leading portion of the intramedullary nail illustrated in FIG. 6;

FIG. 7B is a perspective view of a locking hole at the leading portion of the intramedullary nail, according to another embodiment of the present disclosure;

FIG. 11 is a diagrammatic view showing method steps for implanting the intramedullary nail within the medullary canal of the femur, as illustrated in FIG. 3;

FIG. 12 is a diagrammatic view of method steps for fixating the intramedullary nail to the proximal femur, as illustrated in FIG. 9;

DETAILED DESCRIPTION OF ILLUSTRATIVE EMBODIMENTS

Figures 1, 2:
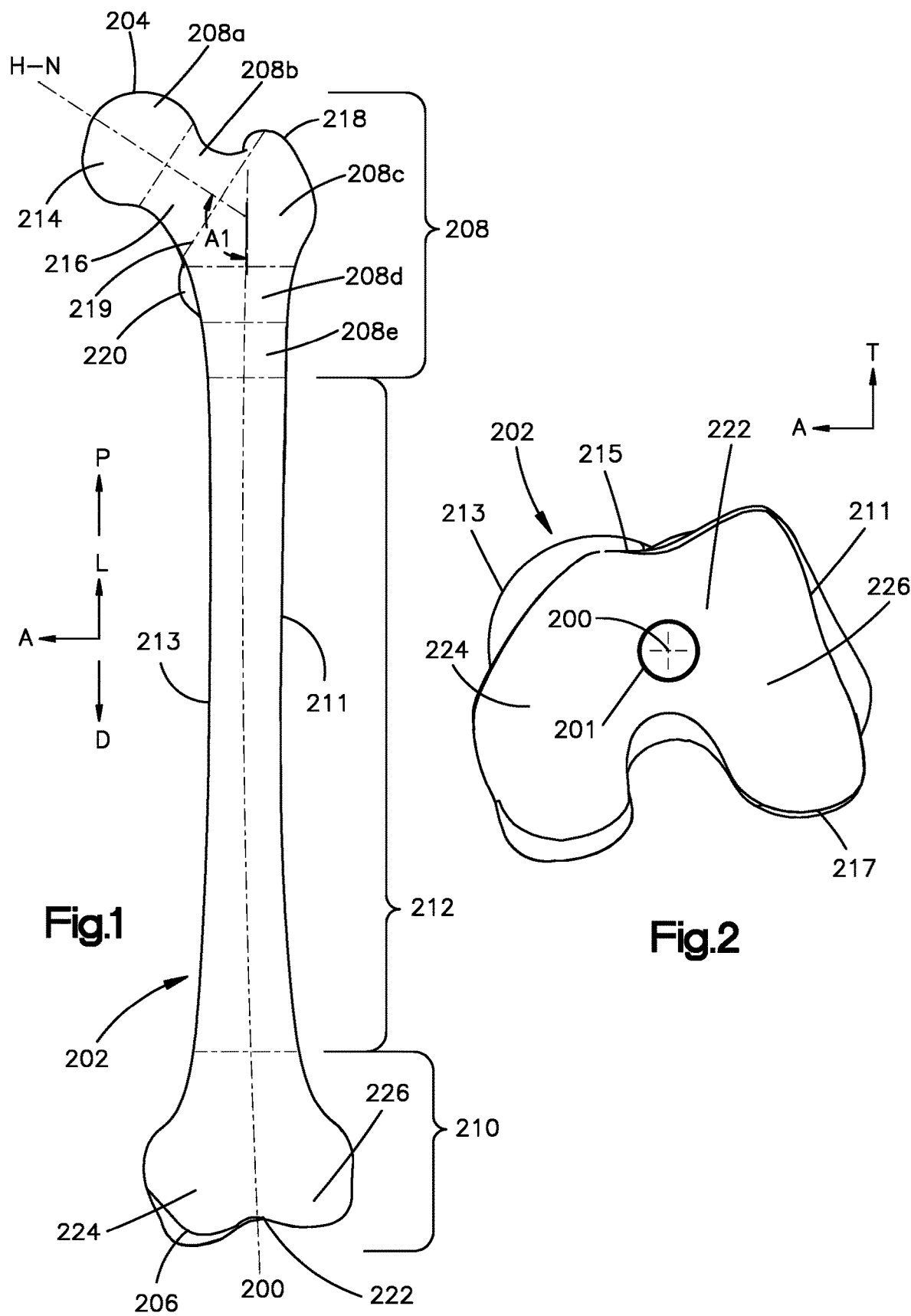
FIG. 1 is an anterior view of a femur.
FIG. 2 is an end view of the distal end of the femur.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, take into account manufacturing tolerances. Further, the terms "approximately" and "substantially" can include 10% greater than or less than the stated dimension or angle. Further, the terms "approximately" and "substantially" can equally apply to the specific value stated.

As used herein with reference to an intramedullary nail or a component thereof, the term "trailing end" refers to the end nearest instrumentation for inserting the nail or component thereof. Similarly, the term "leading end", as used herein with reference to an intramedullary nail or a component thereof, refers to the end that first engages tissue (e.g., bone tissue) as the nail or component thereof is inserted into the femur.

The retrograde intramedullary nails of the present disclosure have features that allow the leading end of the nail to treat factures at proximal portions of the femur, such as for reconstructing subtrochanteric, transtrochanteric, trochanteric, intertrochanteric, and/or femoral neck fractures, in addition to shaft fractures and distal femoral fractures, by way of non-limiting examples. Furthermore, the retrograde intramedullary nails of the present disclosure can allow for prophylactic (i.e., preventative) fixation and support for proximal portions of the femur, such as at the femoral neck. Such prophylactic fixation can be particularly beneficial for higher risk populations, such as osteoporotic and/or obese patients, to reduce the risk of femoral neck fractures.

The retrograde intramedullary nails disclosed herein address technical challenges relating to providing retrograde nails at sufficient dimensions (i.e., lengths and widths/diameters) that can allow fixation at proximal regions of the femur from a retrograde insertion trajectory, including such challenges involving stress concentrations along the leading portion of the nail. For example, the retrograde intramedullary nails disclosed herein include features that reduce stress concentrations at the leading portion of the nail, allowing these retrograde intramedullary nails to be indicated for fractures in the subtrochanteric region and regions anatomically proximally beyond.

Additionally, the following disclosure includes features that facilitate targeting and locking the leading portion of the nail, which features address challenges relating to deflection of the leading portion during insertion within the medullary canal. Also disclosed herein is instrumentation, including an aiming assembly, for targeting and locking the leading portion of the nail.

Referring now to FIGS. 1 and 2, an example of a retrograde insertion trajectory 200 with respect to a femur 202 is shown. The femur 202 has anatomical proximal and distal ends 204, 206 spaced from each other along a longitudinal direction L that is oriented along the anatomical axis of the femur 202. It should be appreciated that the longitudinal direction L is generally oriented along the cranial-caudal direction of patient anatomy. The proximal end 204 is spaced from the distal end 206 in a proximal direction P generally oriented in the cranial or superior direction of patient anatomy. The distal end 206 is spaced from the proximal end 204 in a distal direction D that is generally oriented in the caudal or inferior direction of patient anatomy. It should be appreciated that the proximal and distal directions P, D are each mono-directional components of the longitudinal direction L, which is bi-directional. The femur 202 has a lateral side 211 and a medial side 213 spaced from each other along a lateral direction A, which h is oriented along the medial-lateral direction of patient anatomy. In particular, the medial side 213 is spaced from the lateral side 211 in the anatomical medial direction, and the lateral side 211 is spaced from the medial side 213 in the anatomical lateral direction. It should be appreciated that, as used herein, the term "lateral direction A" is bi-directional and encompasses the mono-directional medial and lateral directions of patient anatomy. The femur 202 also has an anterior side 215 and a posterior side 217 spaced from each other along a transverse direction T, which is oriented along the anterior-posterior direction of patient anatomy. In particular, the anterior side 215 is spaced from the posterior side 217 in the anatomical anterior direction, and the posterior side 217 is spaced from the anterior side 215 in the anatomical posterior direction. It should be appreciated that, as used herein, the term "transverse direction T" is bi-directional and encompasses the mono-directional anterior and posterior directions of patient anatomy. The lateral and transverse directions L, T are each substantially perpendicular to each other and are both offset from the longitudinal direction L.

For purposes of the following disclosure, reference will be made to various anatomical regions of the femur 202, including a proximal region 208, a distal region 210, and a shaft region 212 that extends between the proximal and distal regions 208, 210. It should be appreciated that the proximal region 208 is also referred to herein as the "proximal femur" 208; the distal region 210 is also referred to herein as the "distal femur"; and the shaft region 212 is also referred to herein as the "shaft" 212.

The proximal femur 208 encompasses a plurality of sub-regions, including, for example:
a) a femoral head region 208a, which includes the femoral head 214;
b) an intracapsular region 208b, which includes the femoral neck 216 and extends from the intertrochanteric line 219 to the femoral head 214 along direction having directional components in the proximal direction P and the anatomical medial direction; it should be appreciated that the head-neck axis H-N is offset from the anatomical axis of the femur at a neck angle A1;
c) a trochanteric region 208c, which includes the greater trochanter 218;
d) a transtrochanteric region 208d, which includes the lesser trochanter 220; and
e) a subtrochanteric region 208e, which extends 5 cm below the lesser trochanter 220 in the distal direction D.

In the illustrated example, the retrograde insertion trajectory 200 extends from the distal femur 210 toward the proximal femur 208. In particular, the retrograde insertion trajectory 200 preferably extends from the intercondylar region of the distal femur 210, such as from an entry point 201 at the top of the intercondylar notch 222 between the medial condyle 224 and the lateral condyle 226, toward the proximal end 204. The retrograde insertion trajectory 200 preferably extends along the anatomical axis of the femur 202.

Figure 3:
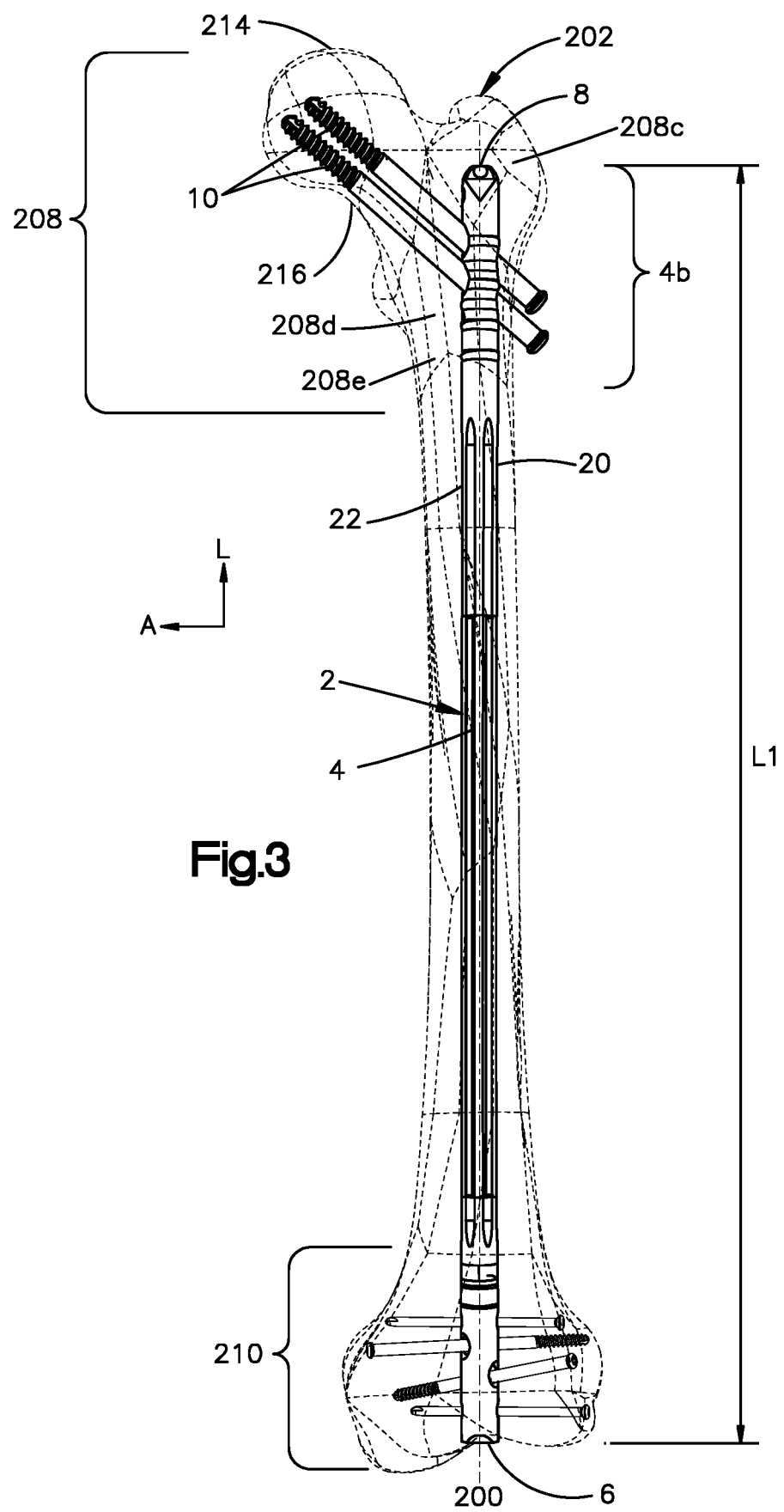
FIG. 3 is an anterior view of the femur having a retrograde intramedullary nail implanted therein.

Referring now to FIG. 3, a retrograde intramedullary nail 2 is shown fully inserted within the medullary canal of a femur along the retrograde insertion trajectory 200. The nail 2 has a body 4 elongate along the longitudinal direction L. The body 4 defines a trailing end 6 and a leading end 8 spaced from each other at a length L1 measured along the longitudinal direction L. As shown, the length L1 can be selected so that the nail 2 extends from the distal condylar region at least to the subtrochanteric region 208e, and can further extend through the transtrochanteric region 208d and to the trochanteric region 208c of the femur 202. At such lengths L1, the nail 2 can be configured so that a leading portion 4b of the body 4 can receive one or more fixation members 10, such as bone screws, that are configured to extend through the body 4 from a lateral side 20 thereof to a medial side 22 thereof and through the femoral neck 216 and into the femoral head 214 for affixing the femoral head 214 and neck 216 to the trochanteric region 208c, or otherwise for providing structural support to the proximal femur 208. The lateral and medial sides 20, 22 of the body 4 are spaced from each other along the lateral direction A.

Referring now to FIG. 4, the body 4 of the retrograde intramedullary nail 2 has a trailing portion 4a (also referred to herein as a "head" 4a of the nail 2) that extends to the trailing end 6 and an intermediate portion 4c (also referred to herein as the "main shaft portion" 4c) that extends between the head 4a and the leading portion 4b, which in turn extends to the leading end 8 of the nail 2. It should be appreciated that, in the field of retrograde intramedullary nails, the leading portion 4b and leading end 8 of the nail 2 are often referred to as the respective "proximal portion" and "proximal end" of the nail 2, with reference to their intended implanted positions being generally at or nearest the proximal region of the bone and generally furthest from the distal region of the bone. Similarly, the trailing portion 4a and trailing end 6 of the nail are often referred to in the field of retrograde intramedullary nails as the respective "distal portion" and "distal end" of the nail 2, with reference to their intended implanted position being generally at or nearest the distal region of the bone and generally furthest from the proximal region of the bone.

The body 4 extends along a central nail axis X, which is preferably curved at least along portions thereof to correspond to the anatomical axis 200 of the femur 202 (see FIG. 3). The body 4 is preferably cannulated along its entire length L1 so that the nail 2 can be advanced along a guide member, such as a guide wire, during insertion into the medullary canal. However, in other embodiments, the body 4 can be non-cannulated or only cannulated along one or more portions thereof. The body 4 defines an exterior surface 12 that extends from the trailing end 6 to the leading end 8 and thus traverses each of the head 4a, main shaft portion 4c, and leading portion 4b of the nail 2. The exterior surface 12 has a cross-sectional shape (i.e., as viewed in a reference plane orthogonal to the central nail axis X) that can be generally circular, which provides the exterior surface 12 with a generally cylindrical shape, although other cross-sectional shapes are within the scope of the present disclosure. The exterior surface 12 has a cross-sectional dimension or width, which can vary along the length of the nail 2 between the trailing and leading ends 6, 8, as described in more detail below. The main shaft portion 4c can define a shaft width W1, measured along a radial direction R perpendicular to the central nail axis X. The shaft width W1 can be characterized as the main width of the nail 2 for classification/selection purposes. The shaft width W1 can be constant, as shown; however, in other embodiments the shaft width W1 can vary, such as by tapering inwardly (diminishing) toward the leading end 8.

The nail body 4 can be constructed of a biocompatible material selected from a group comprising: metal, such as titanium, titanium alloys (e.g., titanium-aluminum-vanadium (TAV) alloys such as Ti-6Al-4V, titanium-aluminum-niobium (TAN) alloys such as Ti-6Al-7Nb, and titanium-molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). The material of the nail body 4 is preferably radiopaque or the nail body 4 can carry radiopaque markers for observation under fluoroscopy to assist the physician during the implantation procedure, including for targeting locking holes of the nail body 4, as described in more detail below. The nail body 4 is preferably monolithic. However, in other embodiment, the body 4 can include two or more separate parts coupled together. By way of a non-limiting example of such a non-monolithic nail body 4, the head 4a and main shaft portion 4c can be monolithic with each other and can be constructed of a TAV alloy, and the leading portion 4b can be constructed of a Ti—Mo alloy. Other non-monolithic combinations are also within the scope of the present disclosure.

Referring now to FIG. 5, the exterior surface 12 can have a primary surface portion 12a that defines the general cross-sectional shape of the nail 2. Accordingly, the shaft width W1 can be measured at the primary surface portion 12a. It should be appreciated that the shaft width W1 (and any of the additional widths described below) can be characterized as a diameter when the primary surface portion 12a defines a generally cylindrical shape at the location where the width is measured.

The exterior surface 12 can also include one or more secondary surface portions or formations that deviate from the primary surface portion 12a. For example, the body 4 can define a secondary formation in the form of a plurality of longitudinal grooves 12b, which can extend along the main shaft portion 4c and optionally along portions of the head 4a and/or the leading portion 4b. The grooves 12b can be configured to reduce stiffness of the nail 2 so as to enhance bone healing, guide insertion of the nail 2 along the medullary canal, distribute stresses (such as by reducing stress concentrations) within the nail body 4, strengthen the nail 2, and/or reduce the overall weight of the nail 2, by way of non-limiting examples. Other formation geometries that deviate from the primary surface portion 12a are also within the scope of the present disclosure.

The head 4a is configured to attach to instrumentation for inserting the nail 2 into the medullary canal. For example, the trailing end 6 can include a mounting formation 14 for mounting to a complementary receiving formation of an instrument, such as an insertion handle. The head 4a can optionally define a head width W2 that is greater than the shaft width W1. The head 4a can also define a taper or "neck" 16 along which the width transitions from the head width W2 to the shaft width W1.

The head 4a also defines one or more trailing locking holes 18 extending through the body 4 along one or more various directions that are offset from the longitudinal direction L. These directions can be perpendicular or oblique to the longitudinal direction L. In the illustrated embodiment, the head 4a defines four (4) trailing locking holes 18, although fewer or more than four (4) holes are also within the scope of the present disclosure. The trailing locking holes 18 are each configured to receive a fixation member, such as a bone screw or a spiral blade, that extends through the respective hole 18 and affixes the head 4a of the nail 2 to the distal femur 210 (see FIG. 3). The trailing locking holes 18 and associated fixation members can also be employed for affixing one or more fractured portions of the distal femur to one another. The trailing locking holes 18 can be targeted, for example, by aiming elements, such as guide holes which in turn may be mated with guide sleeves, carried by or defined through the insertion handle and/or an aiming arm attached to the insertion handle.

The dimensions of the nail 2, such as the length L1 and the widths W1, W2 of the head 4a and the main shaft portion 4c can vary depending on a number of factors, including factors dependent on patient anatomy, such as the dimensions of the femur 202 to receive the nail 2 and the type of retrograde fixation desired (e.g., reconstruction and/or prophylactic). The length L1 can be in a range of about 120 mm to about 500 mm. The shaft width W1 of the main shaft portion 4c can be in a range of about 8 mm to about 16 mm. The width W1 of the head 4a can be in a range of about 8 mm to about 18 mm.

Figure 8:
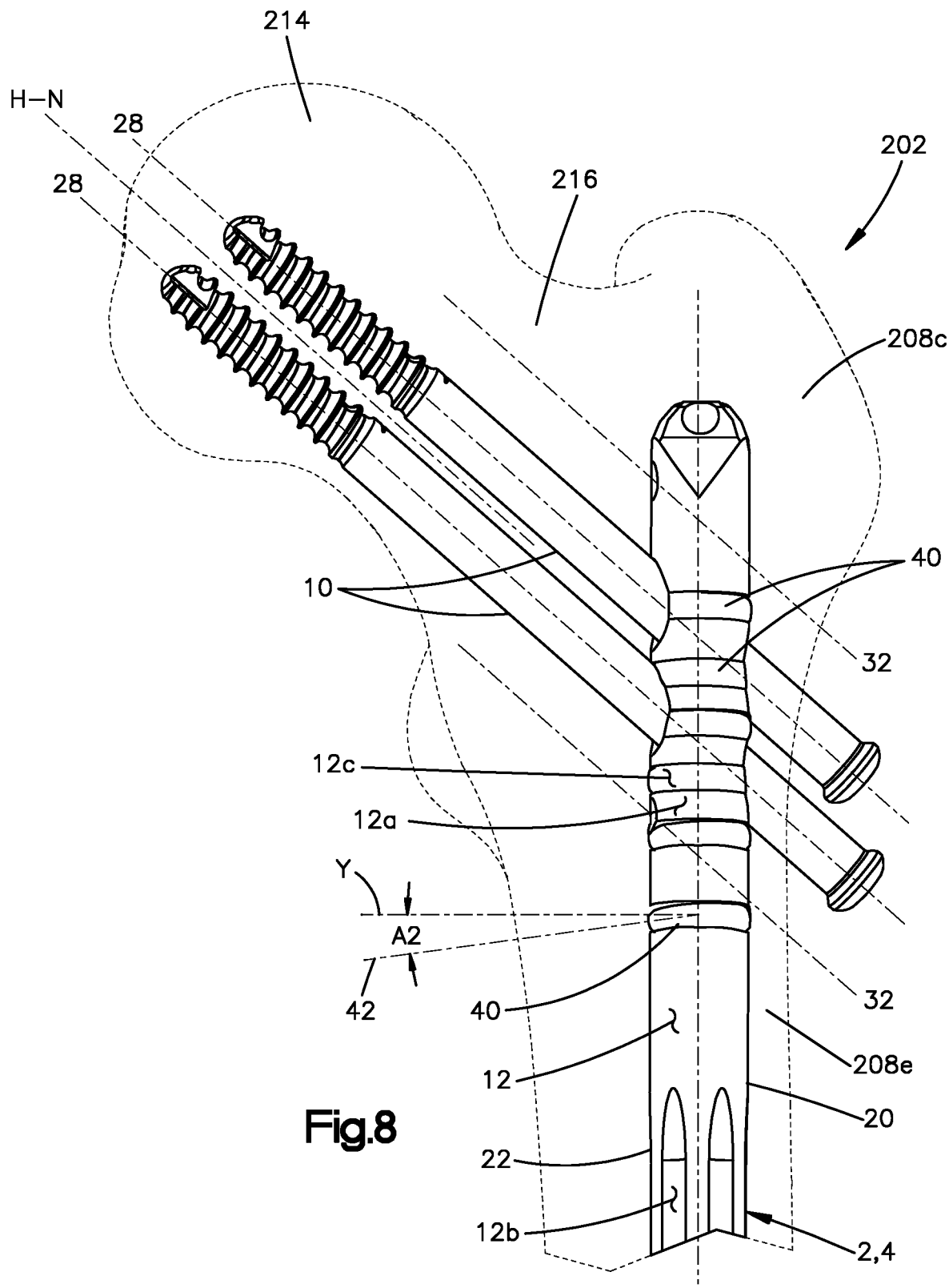
FIG. 8 is an enlarged view of the leading portion of the intramedullary nail illustrated in FIG. 3.

Referring now to FIGS. 6-8, the leading portion 4b of the nail body 4 can define a tapered or canted tip 24 at the leading end 8 for aiding insertion through the medullary canal and into the proximal femur 208 (FIG. 3). The leading portion 4b also defines at least one locking hole 26 that extends through the body 4 from the lateral and medial sides 20, 22 thereof along a respective locking hole axis 28. Each locking hole 26 is configured to receive a corresponding fixation member 10, such as a bone screw or a spiral blade, for affixing the leading portion 4b to the proximal femur 208, such as within or distal to the subtrochanteric region 208e (FIG. 3). It should be appreciated that although the illustrated embodiment shows the leading portion 4b having two (2) locking holes 26, the leading portion 4b can have a single locking hole 26 or more than two (2) locking holes 26.

The leading portion 4b can also define one or more coupling features, such as coupling apertures 30, for coupling an aiming assembly to the leading portion 4b for targeting the locking hole(s) 26. The coupling apertures 30 can extend through the nail body 4, between the lateral and medial sides 20, 22 thereof, along respective aperture axes 32 that are preferably parallel with each other and preferably parallel with the locking holes axes 28. As shown, the leading portion 4b can define two (2) coupling apertures 30 positioned astride the locking holes 26 along the longitudinal direction L, although other configurations are within the scope of the present disclosure. It should also be appreciated that a single coupling aperture 30 or more than two (2) coupling apertures 30 can be employed. The coupling apertures 30 will be discussed in more detail below.

The locking holes 26 are spaced from each other at a hole spacing distance L2, which can be measured from the respective locking hole axes 28 along the longitudinal direction L. As shown in FIG. 8, the locking hole axes 28 can be substantially parallel with the head-neck axis H-N of the femur 202. In other embodiments, one or more of the locking hole axes 28 can be offset at an acute angle from the head-neck axis H-N. As shown in FIG. 7, each locking hole 26 defines a locking hole diameter D1, which can be in a range of about 4.6 mm to about 7.6 mm, and more particularly sized about 5.6 mm or about 6.6 mm. The locking holes 26 can be configured to receive fixation members 10 that are bone screws having a major diameter in a range of about 4.5 mm to about 7.5 mm, and more particularly about 5.5 mm or about 6.5 mm. The bone screws can have lengths in a range of about 24 mm to about 140 mm.

The hole spacing distance L2, the locking hole diameters D1, and the orientation of the locking hole axes 28 can be selected so that each of the corresponding fixation members 10 can extend through the locking holes 26 and through the femoral neck 216, as shown in FIG. 8. Such a configuration can be particularly advantageous for providing prophylactic support for and strengthening of the femoral neck 216, and can also be advantageous for reconstructing femoral neck fractures and/or intertrochanteric fractures. For example, the two (2) fixation members 10 can provide an anti-rotation mechanism that prevents the femoral head 214 and/or neck 216 from rotating with respect to the trochanteric region 208c about the axis 28 of one of the locking members 10.

It should be appreciated, however, that the locking hole(s) of the leading portion 4b can have various configurations and can be adapted for various treatments. For example, although the illustrated locking holes 26 have a circular cross-sectional shape (in a reference plane orthogonal to the locking hole axis 28), other locking hole 26 shapes are within the scope of the present disclosure. For example, one or more of the locking holes 26 can be configured for use with spiral blade type fixation members 10. In other embodiments, one or more of the locking holes 26 can have an oblong cross-sectional shape configured for allowing the associated fixation member 10 to be inserted therethrough at variable angles. Such variable-angle locking member 10 insertion can be particularly beneficial for reconstructing the proximal femur 208. Other variable-angle locking hole 26 configurations are described below. In further embodiments, one or more of the locking holes 26 can be a partial or "semi-hole" at the edge of the leading portion 4b of the nail body 4.

In additional embodiments, one of the locking holes 26 can be adapted to receive a multi-channel fixation barrel that extends through the leading portion 4b and toward the femoral head. The fixation barrel can define a primary channel and a secondary channel, which can be angularly offset from each other. The primary channel is configured to receive a primary fixation member 10, such as a bone screw or bolt, that extends through the barrel and the femoral neck 216 and into the femoral head 214. The secondary channel is configured to receive an additional fixation member, such as an anti-rotation screw that extends through the femoral neck and into the femoral head 214 at an acute angle relative to the primary fixation member 10. In this manner, the secondary fixation member can be configured to prevent subsequent rotation of the femoral head 214 about the axis of the primary fixation member 10.

With continued reference to FIGS. 6-8, the nail body 4 is preferably configured to reduce stress concentrations and increase the strength of the nail 2, particularly at the leading portion 4b thereof. Stress distribution and strength within the leading portion 4b becomes more critical as the nail length L1 increases, particularly for retrograde nails 2 configured treating the proximal femur 208. Accordingly, the leading portion 4b preferably defines at least one relief formation 40 configured to reduce stress concentrations in the body 4, thus strengthening the nail 2 and also increasing its fatigue life. The at least one relief formation 40 can deviate from the primary surface portion 12a in a manner favorably distributing stresses in the leading portion 4b. For example, the at least one relief formation 40 can include a plurality of annular protrusions 40 that extend outwardly from the primary surface portion 12a along a direction away from the central nail axis X, such as the radial direction R. The annular protrusions 40 can be positioned at longitudinal positions along the leading portion 4b that might otherwise exhibit stress concentrations, such as along or adjacent the locking holes 26 and the coupling holes 30. Accordingly, the annular protrusions 40 can intersect at least one and up to all of the locking holes 26 and at least one and up to all of the coupling apertures 30. The annular protrusions each 40 define an outer surface, which can have an arcuate profile in a reference plane extending along the central nail axis X. In other embodiments, one or more of the outer surfaces of the protrusions 40 can have a linear, flat portion, with a leading and/or trailing slope extending from the flat portion at an acute angle with respect to the central nail axis X.

Referring now to FIG. 6, the primary surface portion 12a defines a leading width W3 along the leading portion 4b of the nail body 4. As shown, the leading width W3 can be substantially equivalent to the shaft width W1. The annular protrusions 40 define a width W4 that is greater than the leading width W3 by a factor in a range from about 1.000 to about 1.250 (that is to say, a ratio of W4 to W3 is in a range from about 1.000:1 to about 1.250:1). The annular protrusions 40 also define a longitudinal length L3 and an inter-protrusion spacing distance L4, each measured along the longitudinal direction L. The trailing-most and leading most annular protrusions 40 can be located at respective distances L5 and L6 from the leading end 8 of the nail 2. Distance L5 can be in a range from about 7.5 mm to about 100 mm. The annular protrusions 40 need not extend around the nail body 4 strictly along a path that is orthogonal to the central nail axis X. For example, as shown in FIG. 8, one or more and up to all of the protrusions 40 can extend around the primary surface portion 12a along a path 42 that is oriented at a lead angle A2 from a reference plane Y that extends orthogonal to the central nail axis X. It should be appreciated that the number of annular protrusions 40 and their respective dimensions, including their widths W4, lengths L3 and inter-protrusion spacings L4, lead angles A2, and distances L5, L6 from the leading end 8 can be adjusted as necessary to provide favorable stress distribution within the leading portion 4b of the nail body 4. It should also be appreciated that the dimensions of the annular protrusions 40 can differ between one or more and up to all of the annular protrusions 40. Furthermore, the parameters of the locking holes 26, coupling apertures 30, and the annular protrusions 40 can be adapted as needed to provide beneficial stress distributions within the leading portion 4b of the nail body 4. It should also be appreciated that one or more and up to all of the protrusions 40 can extend less than an entire revolution around the exterior surface 12 (i.e., about central nail axis X). It should further be appreciated that other relief formation geometries can be employed in addition to or as an alternative to annular protrusion(s) 40.

In other embodiments, the leading portion 4b of the nail 2 can be configured such that the leading width W3 differs than the shaft width W1. For example, the leading width W3 can be less than the shaft width W1. In such embodiment, the leading width W3 can taper or otherwise diminish from the shaft width W1 toward the leading end 8 of the nail 2. In yet other embodiment, the leading width W3 can be greater than the shaft width W1. In such embodiments, the nail body 4 can taper outwardly at a transition from the main shaft portion 4c to the leading portion 4b, such that the leading width W3 is greater than the shaft width W1 (at least as measured leading into the transition) by a distance in a range from about 0.01 mm to about 1.50 mm. This outwardly leading taper can terminate at a location trailingly spaced from the trailing-most hole 26, 30 in the leading portion 4b, and is preferably gradual for minimizing stress concentrations at or adjacent the taper.

In further embodiments, as shown in FIG. 7B, one or more of the locking holes 26 can define additional relief formations 40a configured to reduce stress concentrations in the leading portion 4b. For example, the nail body 4 adjacent a periphery of the locking hole 26, particularly at the side of the nail body 4 configured to be positioned toward the lateral wall of the femur 202, can define first and second recesses 45, 47 defining a bump 46 therebetween. The first and second recesses 45, 47 can be milled into the body 4, slightly enlarging the hole 26, although any other forming technique is within the scope of the present disclosure. The first and second recesses can be referred to as a "bump cut", and are more fully described in U.S. Pat. No. 9,427,266, issued Aug. 30, 2016, entitled "BUMP CUT ON HOLE EDGE", the entire disclosure of which is incorporated by reference herein. As shown, the first and second recesses 45, 47 can intersect one or more of the annular protrusions 40 in a manner enhancing the stress relief characteristics of the leading portion 4b of the nail 2.

In additional embodiments, the leading portion 4b can be non-monolithic with the main shaft portion 4c. In such embodiments, the leading portion 4b can be configured to rotate relative to the main shaft portion 4c. For example, the leading portion 4b can be configured to rotate about the central shaft axis X under control of instrumentation, such as a tool insertable within the nail body 4 through the cannulation. In this manner, the rotational position of the leading portion 4b can be rotated to align the locking holes 26 with femoral anatomy as needed.

In further embodiments, the nail body 4 can be configured such that the leading portion 4b flexes directly into the femoral neck 216. In such embodiments, the relief formations can be particularly configured to allow the leading portion 4b to undergo such flexion while maintaining sufficient rigidity to support the femoral neck 216.

Figure 9:
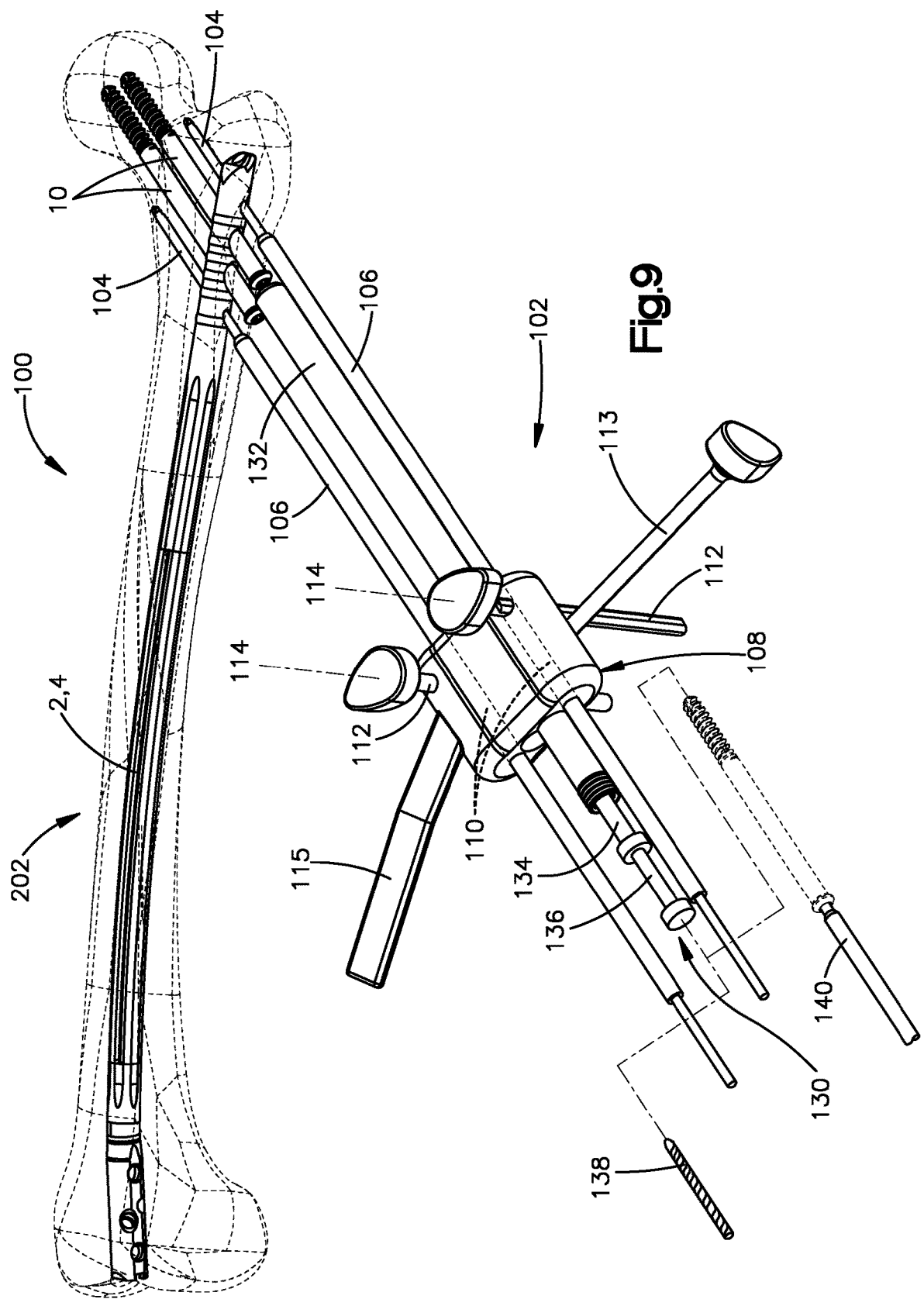
FIG. 9 is a perspective, partially exploded view of an aiming assembly for inserting fixation members through locking holes in the leading portion of the intramedullary nail illustrated in FIG. 3.

Referring now to FIG. 9, a retrograde femoral fixation system 100 can include the intramedullary nail 2 and an aiming assembly 102 for targeting the locking holes 26 at the leading portion 4b of the nail body 4. The aiming assembly 102 can include one or more coupling members, such as guide wires 104, for engagement with the one or more coupling features of the leading portion 4b of the nail body 4, such as the coupling apertures 30 thereof. For example, the guide wires 104 can be configured for insertion within and through the coupling apertures 30. The guide wires 104 are preferably Kirschner wires (also referred to as "k-wires") having a diameter of about 3.2 mm, although other guide wire types and sizes are within the scope of the present disclosure. The physician can use the guide wires 104 for "free-hand" targeting of the coupling apertures 30. The guide wires 104, or at least the leading ends thereof, can be constructed of a radiopaque material, or can carry one or more radiopaque markers, for observation under fluoroscopy to assist the physician in inserting the guide wires 104 through the coupling apertures 30 along the aperture axes 32. The aiming assembly 102 can include guide sleeves 106 that each have a central bore configured to receive one of the guide wires 104. In this manner, the guide sleeves 106 are configured to slide onto the guide wires 104 to provide the guide wires 104 with additional strength and stiffness, for example, after the guide wires 104 have been inserted through the coupling apertures 30.

The aiming assembly 102 can include an aiming guide, such as a guide block 108, that is configured to translate along the guide wires 104 toward the intramedullary nail 2. For example, the guide block 108 can define one or more guide holes 110 configured to align with the coupling holes 30 of the nail 2. The guide holes 110 are each configured to receive a corresponding guide wire 104 therein. For example, the guide holes 110 can be configured for sliding engagement with a corresponding guide sleeve 106 therein, which is, in turn, configured for sliding engagement with a corresponding guide wire 104 therein. In this manner, the aiming block 108 can translate along the guide wires 104 toward the intramedullary nail 2 for targeting the locking holes 26 in the leading portion 4b of the nail body 4. The aiming block 108 preferably includes a handle 115 allowing the physician to manipulate the aiming block 108 as needed. One or more locking members, such as locking pins 112, can extend through the guide block 108 and into communication with the guide holes 110, such that the physician can manipulate the locking pins 112 to affix the position of the guide block 108 with respect to the guide sleeves 106 and guide wires 104. For example, the locking pins 112 can each define a cam surface that engages and disengages the guide sleeves 106 as the locking pins 112 are rotated back and forth, such as about ninety degree (90°) quarter turns about central axes 114 of the locking pins 112.

Figure 10:
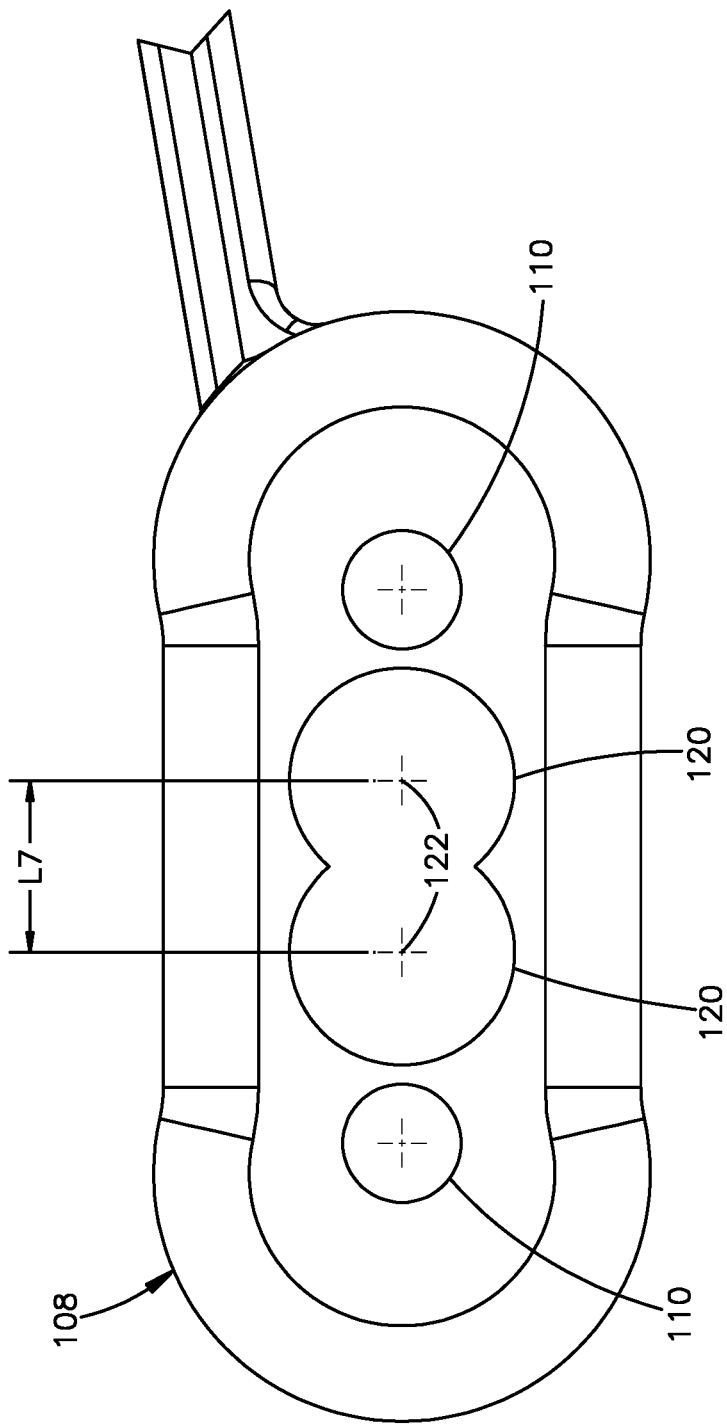
FIG. 10 is an end view of an aiming block of the aiming assembly illustrated in FIG. 9.

The guide block 108 defines at least one aiming channel 120 for targeting the at least one locking hole 26 of the leading portion 4b of the nail body 4. In the illustrated embodiment, the guide block 108 defines two aiming channels 120 that are configured to target two locking holes 26 of the leading portion 4b. Accordingly, as shown in FIG. 10, the aiming channels 120 in the guide block 108 have a channel spacing distance L7, as measured from respective channel axes 122 along a direction perpendicular to the channel axes 122. The channel spacing distance L7 is substantially equivalent to the hole spacing distance L2 at the leading portion 4b of the nail body 4. Moreover, the relative spacing between the guide hole 110 and the aiming channels 120 defined by the guide block 108 is substantially equivalent to the relative spacing between the coupling apertures 30 and the locking holes 26 at the leading portion 4b of the nail body 4. Accordingly, after the guide wires 104 are secured through the coupling apertures 30 of the nail 2 and the guide block 108 is secured to the guide wires 104, the guide block 108 and can be used to target the locking holes 26, which can facilitate more efficient proximal locking, which can also reduce the amount of radiological imaging necessary for proximal locking. As shown, the aiming channels 120 can intersect each other.

The aiming channels 120 can each be configured to receive an insertion device 130 for inserting the fixation members 10 in the locking holes 26. The insertion device 130 can be a multi-part device, such as a three-part trocar combination that includes an outer protection sleeve 132, a drill sleeve 134 insertable through the protection sleeve, and a trocar 136 insertable through the drill sleeve incising soft tissue preferably along the locking hole axis 28 toward the locking hole 26. Operation of the insertion device 130 will be described in more detail below. An additional locking member, such as a locking pin 113, can extend through the guide block 108 and into communication with the aiming channels 120, such that the physician can manipulate the locking pin 113 to affix the position of the outer protection sleeve 132 with respect to the guide block 108.

It should be appreciated that the aiming assembly 102 described above is provided as a non-limiting example of an aiming mechanism for targeting the locking holes 26 at the leading portion 4b. Other types of aiming mechanisms are within the scope of the present disclosure. For example, the nail 2 can be connectable to a swiveling-type aiming arm sleeve, which can swivel about a pivot joint for targeting locking holes 26 that extend along angularly offset axes 28.

Additionally or alternatively, the nail 2 can be connectable to an aiming arm having an adjustment mechanism for providing precise adjustment of the position of its aiming channels along the longitudinal direction L. Such an aiming arm can also be configured to allow controlled deflection along the transverse direction T (i.e., the anterior-posterior direction). In this manner, the aiming arm can be manipulated for adjustable targeting along the longitudinal and transverse direction L, T.

Referring now to FIG. 11, an example method of using the retrograde femoral fixation system 100 for prophylactic (i.e., preventative) treatment 300 for strengthening and supporting the femoral neck 216 will now be described. The physician can perform a step of selecting 302 an appropriate intramedullary nail 2 to provide the desired treatment, that is, a nail 2 having a length L1 such that the leading portion 4b extends at least to the subtrochanteric region 208e such that at least one locking hole axis 28 extends through the femoral neck 216. The physician can determine the appropriate nail length L1 and shaft diameter W2 using techniques known in the art, such as by viewing radiopaque rulers, such as a length ruler and a diameter ruler, placed adjacent the femur 202 under fluoroscopy. The length ruler can be viewed for measuring the length between various landmarks of the femur, such as the length between the top of the intercondylar notch 222 and the intersection of the femoral axis and the intertrochanteric line 219, by way of a non-limiting example. The diameter ruler can be viewed for measuring the diameter of the medullary canal/cortex transition of the femur 202 at one or more locations along the femoral axis. Such measurement can be used to assist the physician in selecting the nail 2 having the desired length L1 and widths (e.g., W1, W2, W3, and/or W4) for insertion.

An additional step includes locating 304 the entry point 201 of the retrograde insertion trajectory, such as an entry point 201 at the top of the intercondylar notch 222, as described above. The physician can then perform a step of inserting 306 a guide member, such as a guide wire, such as a k-wire, into the medullary canal through the entry point 201. With the guide member inserted, the physician can perform a step of opening 308 the medullary canal by advancing a canal-opening device, such as a drill bit and/or an awl, along the guide wire and through the entry point 201 and into the medullary canal. If needed after the opening step 308 (and the canal-opening device has been removed), the physician can optionally perform a canal-expanding or "reaming" step 310 by advancing a reamer along the guide wire and reaming bone tissue to expand the medullary canal in preparation for receiving the nail 2.

After the nail 2 has been selected and the medullary canal has been opened (and optionally reamed), the physician can perform a mounting step 312, whereby the nail 2 is mounted to an insertion handle and is further coupled to the guide wire (or a reaming rod if the optional reaming step 310 was performed). For example, the nail 2 can be assembled over or along the guide wire (or reaming rod). After the mounting step 312, the physician can manipulate the insertion handle for advancing 314 the nail 2 along the guide wire and into the medullary canal. The physician can use the insertion handle to manually insert 316 the nail 2 into the medullary canal as far as practicable by hand. If necessary, the physician can employ an impaction hammer for impacting 318 the insertion handle (such as by delivering hammer blows) to further insert the nail 2 to the final desired longitudinal position within the medullary canal. During the insertion process, the physician can monitor 320 the nail 2 position using fluoroscopy to ensure proper alignment and longitudinal positioning. For example, the physician can use fluoroscopy to determine when the locking holes 26 at the leading portion 4b of the nail body 4 are aligned with the femoral neck 216.

When the physician has determined that the nail 2 is inserted at the desired longitudinal position within the medullary canal, the physician can commence proximal locking 400, i.e., locking the leading portion 4b of the nail body 4 to the proximal femur 208, which will be described in more detail below. After proximal locking 400 is complete, the physician can begin distal locking 322, i.e, locking the trailing portion 4a of the nail 2 to the distal femur 210.

Referring now to FIG. 12, the physician can begin proximal locking 400 by free-hand targeting 402, with the aid of fluoroscopy, one of the guide wires 104 toward one of the coupling apertures 30 along the axis 32 thereof. After the first guide wire 104 has been inserted through the first coupling aperture 30 along the aperture axis 32 and into the far cortex, the physician can advance 404 the first guide sleeve 106 along the first guide wire 104 until, for example, a leading end of the first guide sleeve 106 engages the near cortex in alignment with the first coupling aperture 30. In similar fashion, the physician can free-hand target 406 the second guide wire through the second coupling aperture 30 and into the far cortex and can advance 408 the second guide sleeve 106 along the second guide wire 104 and into engagement with the second coupling aperture 30. With the guide wires 104 and guide sleeves 106 in place, the physician can couple 410 the guide block 108 to the guide sleeves 106 such that the guide sleeves 106 are received in the guide holes 110 of the block 108.

It should be appreciated that, after the first guide wire 104 has been inserted through the first coupling aperture 30 and the first guide sleeve 106 has been advanced along the first guide wire 104, the physician can alternatively couple the guide block 108 to the first guide sleeve 106 and first guide wire 104 before targeting the second guide wire 104 through the second coupling aperture 30. In this manner, the second guide hole 110 of the guide block 108 can provide guided targeting of the second coupling aperture 30. It should be appreciated that the flexion of the leading portion 4b of the nail body 4 (such as during nail 2 insertion in the medullary canal) can potentially reorient one or both of the locking hole axes 28 to a minor extent. Additionally, the first guide wire 104 can also potentially deflect the leading portion 4b as the first guide wire 104 advances through the first coupling aperture 30. Accordingly, during this alternative process for targeting the second coupling aperture 30, the physician can slide the guide block 108 (and the second guide sleeve 106) along the first guide wire 104 toward or away from the nail 2 as needed to reduce or increase the flexibility of the leading portion of the second guide wire 104.

The physician can then perform a step of locating 412 the guide block 108 at a desired targeting distance with respect to the nail 2 by advancing the guide block 108 along the guide sleeves 106 and guide wires 104 toward the nail 2 until the guide block 108 is located at the desired targeting distance, such as when a tip of the outer protection sleeve 132 of the insertion device 130 (disposed in one of the aiming channels 120) contacts the patient's skin or exposed soft tissue. With the guide block 108 located at the desired targeting distance, the physician can affix 414 the guide block 108 to the guide wires 104 and guide sleeves 106 by manipulating the locking pins 112 to their locked positions.

With the guide block 108 affixed at the desired targeting position with respect to the nail 2, the physician can employ the insertion device 130 through the aiming channels 120 of the guide block 108 for inserting 416 the fixation members 10 through the locking holes 26. For example, the physician can advance the trocar 136 through the drill sleeve 134 disposed in the outer protection sleeve 132 so that a leading cutting tip of the trocar 136 makes a stab incision through soft tissue and preferably to the outer surface of the near cortex along an incision path that is substantially aligned with the locking hole axis 28. After the incision is made, the trocar 136 is withdrawn from the drill sleeve 134 and the drill bit 138 is advanced through the drill sleeve 134 for pre-drilling an insertion channel through the near cortex and optionally for extending through the locking hole 26 and pre-drilling an extension of the insertion channel into bone tissue on the far side of the locking hole 26. After the pre-drilling is completed, the drill bit 138 can be withdrawn from the drill sleeve 134, and the drill sleeve 134 can be withdrawn. A driving tool 140 carrying the fixation member 10 at the leading end of the driving tool 140 can then be inserted through the outer protection sleeve 132. The driving tool 140 can advance the fixation member 10 through the outer protection sleeve 132 and, in turn, through the pre-drilled channel in the near cortex, through the locking hole 26, and through the femoral neck 216 until the fixation member 10 is fully seated with respect to the locking hole 26. At this fully seated position, the leading end of the fixation member 10 is preferably purchased within cortical bone of the femoral head 214. After the first fixation member 10 is inserted through the first targeted locking hole 26, the insertion device 130 can be withdrawn from the respective aiming channel 120 and inserted within the second aiming channel 120 for inserting a second fixation member 10 in the second targeted locking hole 26 in like manner. The physician can manipulate the additional locking pin 113 as needed to lock and unlock the insertion device within the first and second aiming channels 120.

Referring again to FIG. 11, after proximal locking 400 is complete, the physician can commence distal locking 322. To facilitate distal locking 322, the physician can attach an aiming arm to the insertion handle, such that guide holes of the aiming arm are aligned with the trailing locking holes 18. Guide sleeves can be inserted within the guide holes of the aiming arm, which aligns central axes of the guide sleeves with the trailing locking holes. Similar to the proximal locking step 400 described above, the physician can advance a cutting device, such as a trocar, through the guide sleeve and can make a stab incision through soft tissue and preferably to the outer surface of the near cortex along an incision path that is substantially aligned with the trailing locking hole 18. The physician can withdraw the cutting tool and then advance a drill bit through the guide sleeve for pre-drilling an insertion channel through the near cortex and optionally for extending through the trailing locking hole 18 and pre-drilling an extension of the insertion channel into bone tissue on the far side of the trailing locking holes 18. After pre-drilling, the physician can advance a driving tool carrying a fixation member, such as a bone screw and/or spiral blade, through the guide sleeve and, in turn, through the pre-drilled hole in the near cortex and into the trailing locking hole 18 and, optionally, into the far cortex of the distal femur 210. It should be appreciated that the guide sleeves of the aiming arm can be configured for use with the insertion device 130 described above to perform the incising, pre-drilling, and driving steps of distal locking 322. It should also be appreciated that distal locking 322 can optionally be performed prior to proximal locking 400.

It should be appreciated that the example method described above can also be adapted for treating femoral fractures (e.g., femoral reconstruction), including fractures at any and each of the distal femur 210, shaft 212, and proximal femur 208, in addition or alternative to prophylactic strengthening and support of the femoral neck. For example, to treat femoral fractures, the physician can perform additional, preliminary steps that can include: identifying the fracture site(s); reducing the fracture(s); and identifying one or more desired fixation members (e.g., bone screws and/or spiral blades) and associated approaches for fixating the fractured portion(s) of the femur. The step of selecting 302 the appropriate intramedullary nail 2 can include selecting a nail 2 having one or more locking holes respectively sized for such fixation member(s) and aligned with such approach(es).

It should be also appreciated that the foregoing methods are provided as examples, and that the physician can elect to adjust the sequence of various steps, omit one or more of the steps, and/or perform one or more additional steps, as needed.

Figure 13A:
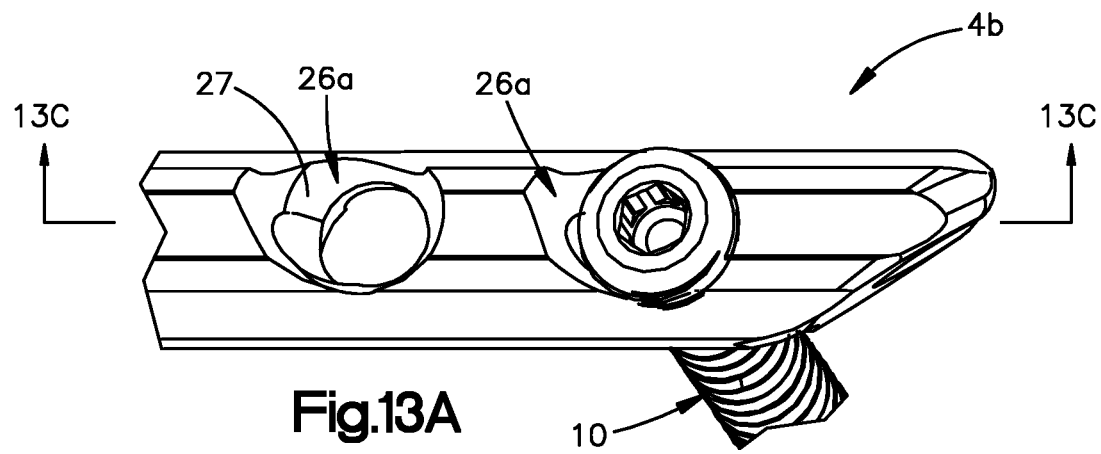
FIGS. 13A and 13B are perspective views of variable-angle locking holes defined in a leading portion of an intramedullary nail similar to the nail illustrated in FIGS. 3-9, with a fixation member seated in one of the variable-angle locking holes.
Figure 13B:
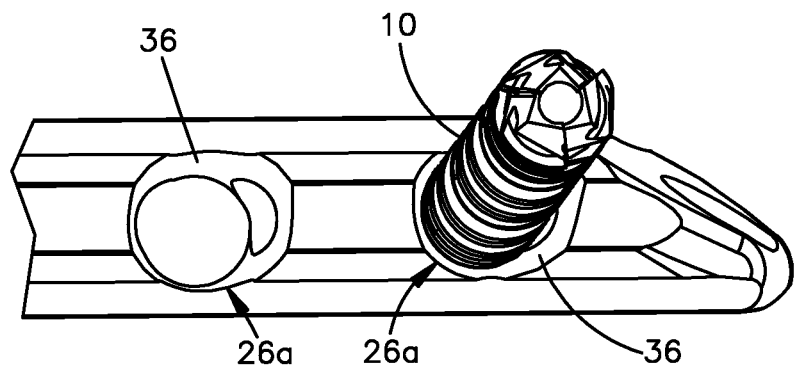
Figure 13C:
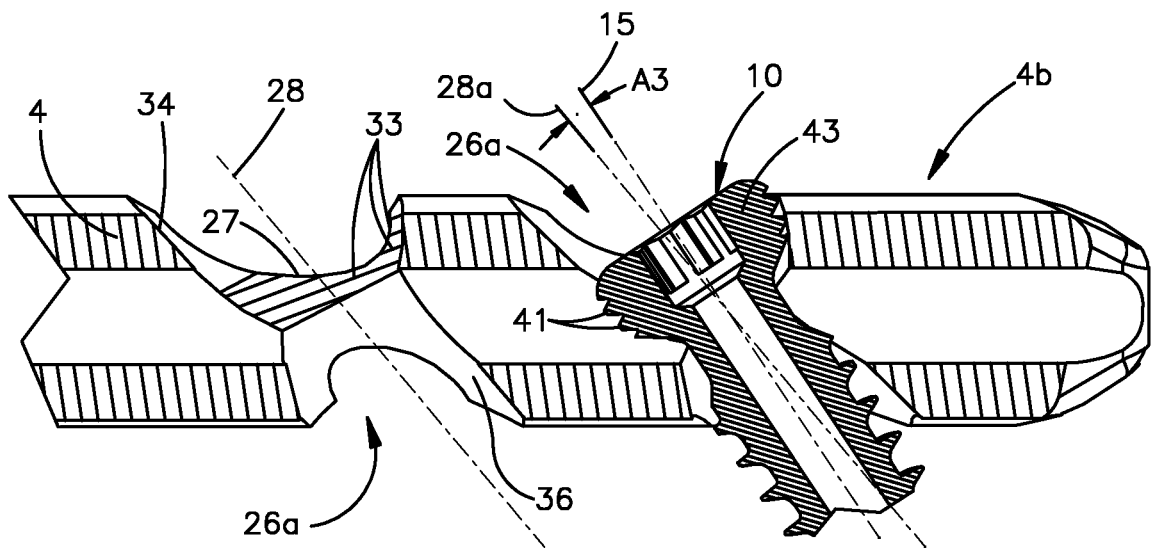
FIG. 13C is a sectional side view of the variable-angle locking holes taken along section line 13C-13C in FIG. 13A, and illustrating a fixation member inserted at angulation through one of the variable-angle locking holes illustrated in FIGS. 13A and 13B.

Referring now to FIGS. 13A-13C, one or more of the locking holes in the leading portion 4b of the nail 2 can be a variable-angle locking hole 26a. Such variable-angle ("VA") locking holes 26a are configured such that a fixation member 10, such as a bone screw, can be inserted through the hole 26a at angulation (i.e, an angle A3 at which a central axis 15 of the fixation member 10 is offset from the central hole axis 28a, as shown in FIG. 13C) and affixed with respect to the hole 26a at the angulation. As shown, within the VA locking hole 26a, the nail body 4 defines an interior surface 27 that provides a VA locking structure, which can include a plurality of lobes or columns circumferentially spaced from each other by a plurality of recesses (which can also be referred to as "key cuts") located circumferentially between the columns. The VA locking structure of the interior surface 27 can include internal or "hole" threads 33 (see FIG. 13C) that traverse the columns and can also traverse portions of the recesses. The internal threads 33 can extend in uninterrupted fashion about the circumference of the interior surface 27, although the internal threads 33 can optionally be circumferentially interrupted by the recesses. The internal threads 33 can extend helically (i.e., at a helix angle) along one or more helical splines or thread paths about the central axis 28 of the locking hole 26a.

The hole threads 33 are configured to threadedly engage (i.e., intermesh with) external threads 41 defined on the head 43 of the fixation member 10 (which threads 41 can also be referred to as "head threads" 41) as the head 43 advances within the VA locking hole 26a at either a nominal orientation (i.e., the central axis 15 of the fixation member 10 is colinear with the central hole axis 28a) or at an angulation within a predetermined angulation range. The head 43 of the fixation member 10 can be configured for VA insertion and locking within the VA locking hole 26a. For example, the head 43 can have curved, convex profile that allows the head threads 41 to threadedly engage the hole threads 33 at both a nominal orientation and at angulation. Furthermore, head 43 and the interior surface 27 can be cooperatively configured such that hole threads 33 and/or the head threads 41 deform as the head 43 advances within the VA locking hole 26a, thereby locking the position of the fixation member 10 with respect to the nail body 4. The nail body 4 also preferably defines at least one lead-in surface 34 and at least one undercut surface 36, that extend respectively from the outer surface of the nail body to the interior surface 27. The lead-in and undercut surfaces 34, 36 provide space for the head 43 and shaft of the fixation member 10 at angulated positions.

The VA locking holes 26a of the present embodiment allow the physician to select an advantageous angulation for the fixation member 10 through the hole 26a, which can be beneficial for inserting the fixation member 10 into a fractured portion of the proximal femur 208. Angulated insertion also allows the fixation members 10 to extend through the VA locking holes 26a and favorably through the femoral neck and into the femoral head even when the leading portion 4b of the nail 2 is slightly off its intended position and/or orientation in the medullary canal.

It should be appreciated that the VA locking holes 26a can have a circular hole profile, as viewed in a reference plane orthogonal to the central hole axis 28a. Alternatively, the VA locking holes 26a can have other hole profile shapes, such as a polygonal shape, such as a trigon shape that includes three (3) columns (that form the sides of the trigon) and three (3) recesses (that form the corners of the trigon) spaced between the columns. The polygonal and trigon holes can be configured as more fully described in U.S. Patent Publication No. 2021/0015526A1, published Jan. 21, 2021, entitled "DEFORMABLE THREADED LOCKING STRUCTURES, AND RELATED SYSTEMS AND METHODS," the entire disclosure of which is incorporated by reference herein.

It should be appreciated that although the features disclosed above have been described with reference to retrograde insertion into a femur, the features of the intramedullary nail and related instrumentation described herein can also be employed for use with other longbones, including the humerus, radius, ulna, tibia, and fibula.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A retrograde intramedullary nail for retrograde insertion in the medullary canal of a femur, comprising:
   a body that is elongate and defines a leading end and a trailing end spaced from each other at a length sufficient to extend from an intercondylar region of the femur at least to a subtrochanteric region of the femur, the body further defining a leading portion that extends to the leading end,
   wherein the leading portion defines at least one locking hole configured to receive a fixation member, wherein the at least one locking hole defines a central hole axis, and the leading portion is configured such that the central hole axis extends through the neck of the femur and intersects the head of the femur, and
   wherein the body defines,
      an exterior surface having a primary surface portion that is substantially cylindrical within the leading portion; and
      at least one relief formation that deviates from the primary surface portion and is configured to reduce stress concentrations in the leading portion, wherein the at least one relief formation comprises a plurality of annular protrusions that extend outwardly from the primary surface portion.

2. The retrograde intramedullary nail of claim 1, wherein the at least one locking hole intersects at least one of the plurality of annular protrusions, the body adjacent a periphery of the at least one locking hole defines first and second recesses defining a bump therebetween along the periphery.

3. The retrograde intramedullary nail of claim 1, wherein the plurality of annular protrusions define respective cross-sectional dimensions that are greater than a cross-sectional dimension of the primary surface portion within the leading portion by a factor in a range from 1.001 to about 1.250.

4. The retrograde intramedullary nail of claim 3, wherein a trailing-most one of the plurality of annular protrusions is spaced from the leading end by a distance is in a range from about 7.5 mm to about 100 mm.

5. The retrograde intramedullary nail of claim 1, wherein the body further defines:
   a trailing portion that extends to the trailing end; and
   an intermediate portion that extends between the trailing and leading portions,
   wherein the primary surface portion defines a first diameter within the intermediate portion and a second diameter within the trailing portion, wherein the second diameter is greater than the first diameter.

6. The retrograde intramedullary nail of claim 1, wherein the at least one locking hole comprises two locking holes each extending through the body along respective central hole axes that are each substantially parallel with the head-neck axis of the femur.

7. The retrograde intramedullary nail of claim 1, wherein the body defines internal threads within the at least one locking hole, and the internal threads are configured to engage complementary external threads at a head of the fixation member for threaded fixation of the at least one fixation member to the retrograde intramedullary nail.

8. The retrograde intramedullary nail of claim 7, wherein the at least one locking hole extends through the body along at least one respective hole axis, and the body defines, within the at least one locking hole, a plurality of columns circumferentially spaced from each other around the hole axis by a plurality of recesses, the internal threads traverse the plurality of columns, and the plurality of columns are configured for variable-angle insertion of the fixation member through the at least one locking hole.

9. A system for femoral fixation, comprising:
   an intramedullary nail having a body that is elongate and defines a leading end and a trailing end spaced from each other at a length sufficient to extend from an intercondylar region of the femur at least to a subtrochanteric region of the femur, wherein a leading portion of the body extends to the leading end and defines 1) at least one locking hole configured to receive at least one fixation member for affixing the leading portion to the femur, and 2) at least one relief formation configured to reduce stress concentrations in the leading portion, the body further defining an exterior surface having a primary surface portion that is substantially cylindrical within the leading portion, wherein the at least one relief formation deviates from the primary surface portion and comprises a plurality of annular protrusions that extend outwardly from the primary surface portion; and
   an aiming assembly configured to connect to the leading portion and insert at least one fixation member through the at least one locking hole.

10. The system of claim 9, wherein:
    the leading portion defines two or more coupling apertures positioned astride the at least one locking hole with respect to a longitudinal direction of the intramedullary nail; and
    the aiming assembly comprises:
       two or more guide wires for insertion within the two or more coupling apertures; and
       an aiming block having 1) two or more guide slots for guiding translation of the aiming block along the two or more guide wires, and 2) at least one aiming channel for guiding movement of the at least one fixation member toward the at least one locking hole.

11. The system of claim 10, wherein the at least one targeting hole is located between the two or more guide slots along a direction parallel to the longitudinal direction.

12. The system of claim 10, further comprising two or more guide sleeves insertable along the two or more guide slots, wherein the two or more guide sleeves each define a central bore sized for insertion of the respective guide wire therethrough.

13. The system of claim 10, further comprising an insertion device insertable through the at least one aiming channel, wherein the insertion device is configured to insert at least one fixation member through the at least one locking hole in the leading portion of the nail body.

14. The system of claim 13, wherein:
the at least one locking hole comprises first and second locking holes spaced from each other at a hole spacing distance along the longitudinal direction;
the at least one fixation member comprises a first fixation member and a second fixation member;
the at least one aiming channel of the guide block comprises first and second aiming channels spaced from each other at a spacing distance equivalent to the hole spacing distance; and
the insertion device is configured to extend, selectively and sequentially, through each of the first and second aiming channels, and the insertion device is further configured to 1) advance the first fixation member through the first aiming channel and subsequently through cortical bone tissue on a near side of the first locking hole, through the first locking hole, and subsequently into cortical bone tissue on a far side of the first locking hole, and 2) advance the second fixation member through the second aiming channel and subsequently through cortical bone tissue on a near side of the second locking hole, through the second locking hole and subsequently into cortical bone tissue on a far side of the second locking hole.

* * * * *